(12) United States Patent
Luckert

(10) Patent No.: US 9,915,656 B2
(45) Date of Patent: Mar. 13, 2018

(54) HAND-HELD MEASURING INSTRUMENT AND PROCEDURE FOR THE DETECTION OF MOLD ATTACK IN INTERIOR SPACES

(71) Applicant: Robert Bosch GmbH, Stuttgart (DE)

(72) Inventor: Katrin Luckert, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 697 days.

(21) Appl. No.: 14/478,979

(22) Filed: Sep. 5, 2014

(65) Prior Publication Data

US 2015/0072358 A1    Mar. 12, 2015

(30) Foreign Application Priority Data

Sep. 6, 2013 (DE) ........................ 10 2013 217 822

(51) Int. Cl.
*G01N 33/569* (2006.01)
*C12Q 1/24* (2006.01)

(52) U.S. Cl.
CPC ......... *G01N 33/56961* (2013.01); *C12Q 1/24* (2013.01); *G01N 2400/24* (2013.01)

(58) Field of Classification Search
None
See application file for complete search history.

(56) References Cited

U.S. PATENT DOCUMENTS

| | | |
|---|---|---|
| 2004/0017570 A1 | 1/2004 | Parikh et al. |
| 2011/0039280 A1* | 2/2011 | Leary ................. G01N 21/253 |
| | | 435/7.32 |

FOREIGN PATENT DOCUMENTS

| | | |
|---|---|---|
| DE | 10 2010 031 051 A1 | 9/2011 |
| DE | 10 2010 064 251 A1 | 6/2012 |
| WO | 2007/092302 A2 | 8/2007 |
| WO | 2008/156415 A1 | 12/2008 |
| WO | 2012/089417 A1 | 7/2012 |

OTHER PUBLICATIONS

Machine-generated translation of WO2012089417, retrieved from https://worldwide.espacenet.com/ on Jul. 7, 2017 (10 pages).*
Carson, M.A.; Bargeron, C.B.; Benson, A.B.; Fraser, A.B.; Phillips, J.T.; Groopman, J.D.; Strickland. P.T.; Ko, H.W.; An automated, handheld biosensor for aflatoxin. Biosenors & Bioelectronics. 2000. 841-848. 14. Elsevier.

* cited by examiner

*Primary Examiner* — Christine Foster
(74) *Attorney, Agent, or Firm* — Maginot, Moore & Beck LLP

(57) ABSTRACT

A hand-held measuring instrument is used for detecting hidden mold damage in interior spaces. The measuring instrument includes at least one collection unit configured to intake at least of one interior space sample, at least one buffer unit, at least one immunological test unit, an evaluation unit and a control panel. The at least one buffer unit has a first compartment and a second compartment.

7 Claims, 1 Drawing Sheet

HAND-HELD MEASURING INSTRUMENT AND PROCEDURE FOR THE DETECTION OF MOLD ATTACK IN INTERIOR SPACES

This application claims priority under 35 U.S.C. § 119 to patent application number DE 10 2013 217 822.0, filed on Sep. 6, 2013 in Germany, the disclosure of which is incorporated herein by reference in its entirety.

BACKGROUND

The present disclosure relates to a procedure for the detection of hidden mold damage in interior spaces. The present disclosure furthermore relates to a hand-held measuring instrument for carrying out the detection procedure.

Mold attack in interior spaces and mold damage resulting therefrom occur even in new buildings and can be connected with health consequences going back to mold spores. To test interior spaces for mold attack, various detection methods are used. Thus mold spores can be collected from the indoor air or dust collections by filtration or impaction and subsequently cultured, for example, for 7 days in the laboratory, after which detection takes place with the aid of the culture. However, even in the case of obvious fungal attack a large quantity of spores must be collected and cultured for several days. Likewise, microscopic investigations can be carried out on particle collections, unculturable spores also being detected. Besides these classical laboratory tests, "do-it-yourself" quick tests are known. Devices and procedures for the investigation of mold attack are known in the prior art. A hand-held measuring instrument and a procedure for the detection of hidden mold damage in interior spaces is known, for example, from the document DE 10 2010 064 251 A1.

As before, however, the sample preparation is an important part of the overall analysis process of a real sample, in particular if only small amounts of an analyte can be determined in the air.

SUMMARY

The subject of the present disclosure is a hand-held measuring instrument for the detection of hidden mold damage in interior spaces, containing the following components:
  at least one collection unit for the intake at least of one interior space sample,
  at least one buffer unit,
  at least one immunological test unit,
  an evaluation unit, and
  a control panel,
the buffer unit having a first compartment and a second compartment.

The present disclosure also relates to a procedure for the detection of hidden mold damage in interior spaces using the hand-held measuring instrument described beforehand, comprising the following procedure steps:
  a) collection of an interior space sample,
  b) taking up of the sample in a buffer,
  c) immunological testing of the buffered sample,
  d) evaluation of the immunological test, and
  e) display of the test result from step d),
where in the sample taken up in a buffer in step b), one or more analyte(s) is concentrated before the immunological testing in step c).

A compartment within the meaning of the present disclosure can in particular be a broadly delineated space. This can be made available by a division of the buffer unit. The buffer unit has at least a first and a second compartment, but can also have three or more compartments.

The essence of the disclosure is a concentration of the sample preceding the measurement. The sample, in particular aspirated interior space air, is collected in a collection unit. Subsequently, the sample is taken up in a buffer. Before the immunological measurement, according to the disclosure a sample concentration is carried out in the buffer unit. For this, the buffer unit of the hand-held measuring instrument is compartmentalized.

The advantages of the disclosure lie in the fact that the subsequent measurement can be carried out directly. By this means, lengthy collection procedures are shortened. The sample amount is controlled, in particular, by the strength of the airflow and the duration of the sample collection. The concentration during the sampling can on the one hand specifically enrich the target analyte, fungal spores, on the other hand a preliminary purification can be carried out by this means. Non-analytes can thus be separated off. By this means possible interfering effects can be reduced. In particular, the sample can be provided in higher concentration by an affinity purification and a specific measuring buffer for the measurement can be provided. All in all, by means of the concentration in the context of sample preparation, an important step for the subsequent analysis is made available, which significantly facilitates the detection of mold spores. This is essential, in particular, for the implementation of a rapid test. The disclosure enables a semiquantitative rapid test to be employed for rapid on-site detection of mold spores from air and dust samples. The amount of sample necessary for this can be enriched rapidly and specifically from not very concentrated media such as air. This makes available a basis for a portable measuring instrument independently of conventional laboratory analysis.

The sample is firstly admitted to a collection unit of the hand-held measuring instrument. For this, constituents of building materials such as wall-coverings, plaster dusts or the like are manually applied to a support within the apparatus. However, a collection unit according to the impaction and/or filtration procedure is preferred. Accordingly, the collection unit preferably has a baffle plate and/or a filter. The baffle plate is a carrier plate, which is coated with an adhesive for adhesion of the fungal constituents. For the filtration of the air, special filter membranes are employed which are suitable for the filtration of molds or their constituents such as spores. Here, the particles situated in the air with a size from approximately 0.5 µm are deposited and collected on the filter membrane. To generate an airflow, the collection unit preferably has an air intake module, e.g. in the form of a pump or of a ventilator. The air intake flow can be about 100 l/min Even dusts can be deposited and collected from the air in this way. In order to avoid contamination, the actual collection unit, i.e. the baffle plate or the filter, is inserted into the apparatus as a single-use component.

The collected sample is taken up in a buffer solution. The collection unit downstream is correspondingly a buffer unit. The collected sample is transferred to a first compartment of the buffer unit. Binder molecules present for the analyte, the fungal spores, are dissolved in the buffer. After the addition, fungal spores present are bound by the binder molecules and are present in solution as a complex. The solution is transferred to the second compartment of the buffer unit. The complex of binder molecule and fungal spore is immobilized there. Within the framework of one embodiment, the second compartment of the buffer unit has a solid phase for the immobilization of the binder molecule-analyte complex. A solid phase within the meaning of the present disclosure can in particular be a nonaqueous matrix, to which the binder molecule can adhere. The solid phase can be a purification column or a discontinuous phase. The solid phase preferably comprises a carboxylated surface. On this carboxylated surface is immobilized a further binding molecule, which specifically binds the first binding molecule and thus the complex of first binding molecule and analyte to the solid phase.

If antibodies which are directed specifically against surface markers of mold spores, such as β-glucans, are used as the first binder molecule (primary antibody), the second binding molecule can an antibody (secondary antibody), which is directed species-specifically itself against the primary antibody. The secondary antibody must already be present immobilized. This can take place covalently on a carboxylated surface, for example, by means of coupling reagents such as s-NHS and EDC (N-hydroxysulfosuccinimide and carbodiimide) as an amide bond. Non-bonded molecules in the sample can be removed by addition of a rinsing solution. Subsequently, the mold spores bound by means of the binder molecule can be eluted by means of a further buffer and brought into solution again.

At least one buffer cartridge, more suitably two or more buffer cartridges, is/are situated in the buffer unit. In the context of one embodiment, the buffer unit of the hand-held measuring instrument can have at least three cartridges for buffer. The buffer cartridges can in particular contain different buffers. For example, a first buffer cartridge can contain a buffer which contains binder molecules in solution, a second buffer cartridge can contain a buffer without binder molecules. This can be used for rinsing the solid phase or for removing unbound constituents. A third buffer cartridge can contain an "elution buffer", which serves for the removal of the bound analyte. It can also be provided that the binder molecules are added separately. For this purpose, a further cartridge can be provided. The addition of further test components with the aid of additional cartridges or a fluid system to be attached separately for the storage and metered addition of appropriate components is also possible.

In a separate embodiment, the collection unit and the buffer unit are combined to give one unit such that the collection of the sample and the uptake in the buffer takes place simultaneously. The cartridges containing buffer solution can likewise be configured as a single-use component and are employed in the measuring instrument together or separately with the collection unit. In order that the collected sample is taken up in a buffer solution, the buffer cartridge must firstly be opened. This takes place either automatically, as soon as the sampling is concluded, or is explicitly operated by the user. Correspondingly, the addition of the further buffers from the respective cartridges can take place as an automated sequence, or in each case be operated by the user. To improve the uptake and the mixing of the sample in the buffer solution, a separate mixing can take place, which takes place, for example, with mechanical auxiliaries.

The sample is transferred from the buffer unit to the immunological test unit. Depending on implementation of the immunological test, the test unit can contain components for reagent addition, preferably a reagent cartridge, or lateral-flow test components. In the lateral-flow test, a direct determination of the analytes takes place. The immunological test unit is preferably used as a one-time test, such that a replacement of the test components in the form of a test strip and/or of a reagent cartridge takes place for each measurement. Alternatively, the test unit can also be used several times, such that a replacement after each individual measurement is not applicable. All in all, the baffle plate and/or the filter, the buffer cartridges, the reagent cartridge or the lateral-flow test components can be configured in different combination or individually as single-use components and correspondingly be inserted into or attached to the hand-held measuring instrument individually or in combination.

Differing transduction principles, e.g. in the form of optical or electrical signals, are suitable for the immunological test. Preferably, the evaluation of the immunological test is carried out by electronic or optical sensors. The evaluation unit therefore preferably has a photometric or electronic transduction module. The functioning depends on the respective measuring principle. Thus a photometric analysis of the sample, for example, but also an impedance measurement or a fluorimetric measurement is possible. Generally, the apparatus enables the parallel determination of a number of antigens or haptens by means of one or more immune tests. For example, multi-analyte-capable lateral flow tests (LFT) are available for this purpose. Labelled detection antibodies can either already be initially introduced in the buffer solution or immobilized on the receiving surface of the test unit. If appropriate antigens or haptens are present in the sample, the antigen-antibody conjugates resulting thereby bind to the corresponding detection areas, which are then read optically or otherwise by means of the evaluation unit. Those antigens or haptens can be determined which are characteristic for molds in general, such as, for example, ergosterol or beta-1,3-glucan. The presence of these substances indicates that molds are present in the sample. In addition, those antigens or haptens can be determined which are characteristic of specific mold species, e.g. determined surface antigens of fungal spores. Such differentiated analyses allow conclusions on whether with great probability the fungi were carried in from outside, or whether they originate from interior space damage. As species characteristic for interior attacks, for example, the following fungal spores can be measured: *Acremonium* spp., *Aspergillus penicillioides, Aspergillus restrictus, Aspergillus versicolor, Aureobasidium pullulans, Chaetomium* spp., *Phialophora* spp., *Scopulariopsis brevicaulis, Scopulariopsis fusca, Stachybotrys chartarum, Tritirachium* (*Engyodontium*) *album* or *Trichoderma* spp.

The display of the test result can take place in differing form. Preferably, the display of the test result takes place by means of a control panel. In a photometric evaluation, the result can be read off immediately with the aid of one or more characteristic color changes or discolorations, which optionally make possible a qualitative or semiquantitative statement on matching with a color scale. Thus a quick statement in the form of "not detectable", "slight contamination" or "high contamination" is possible. Alternatively, the apparatus carries out an optical or electrical evaluation internally, which is indicated qualitatively, semiquantitatively or quantitatively as a result by an electronic indicator, e.g. by means of a display or individual LEDs. Moreover, the apparatus preferably has a control indicator, which confirms the correct carrying out of the test or if appropriate suggests possible sources of error. The apparatus can be operated both using accumulators as well as using conventional batteries.

The present disclosure further relates to a procedure for the detection of hidden mold damage in interior spaces using the hand-held measuring instrument described beforehand, comprising the following procedure steps:

a) collection of an interior space sample, b) taking-up of the sample in a buffer,
c) immunological testing of the buffered sample,
d) evaluation of the immunological test, and
e) display of the test result from step d), where in the sample taken up in a buffer in step b), one or more analyte(s) is concentrated before the immunological testing in step c).

The essence of the procedure is a concentration of the sample preceding the immunological measurement. Advantages of the procedure lie in the fact that, on the one hand, the target analytes from the air can be selectively bound and thus a concentration of the target analytes can be achieved, and in addition in that interfering constituents can be removed from the sample, such that cross-sensitivity reactions are reduced. In particular, by means of an affinity purification the sample can be introduced in a higher concentration and a special measuring buffer. All in all, by means of the concentration in the context of the sample preparation a significant facilitation for the subsequent analysis for the detection of mold spores is made available. The amount of sample can be enriched rapidly and specifically from lowly concentrated media such as air. Thus the procedure according to the disclosure enables within a measurement system the detectability of an analyte, which otherwise is not present in adequate concentration for a measurement.

In a first step, in particular, air is aspirated and collected by a collection device. Here, the collection of the sample can be carried out by the impaction or filtration procedure, i.e. with the aid of adhesive- coated baffle plates or using suitable filter membranes. Subsequently, the sample is taken up in a buffer solution. The collection of the sample and the taking-up of the sample in the buffer or the buffer solution can take place simultaneously, such that the sample is suspended in the buffer even during the collection process. For better distribution of the sample, after the uptake of the sample in the buffer a thorough mixing of the solution can be carried out. Here, the buffered sample, for example, can be thoroughly mixed mechanically by vibration or stirring.

Within the meaning of the present disclosure, a buffer can in particular be a buffered solution, which opposes changes in the pH by action of a conjugated acid/base pair. Preferably, a buffer provides physiological conditions for the analyte.

According to the disclosure, the analyte or analytes is/are concentrated in the sample taken up in a buffer before immunological testing. In the context of one embodiment, the concentration can be carried out by means of analyte-specific binder molecules. In the context of a further embodiment, the binder molecules can be antibodies or complexing agents which specifically bind the analyte(s). In the case of mold spores as analytes, these can be antibodies which are directed specifically against surface markers of mold spores such as β-glucans. The term "antibody" within the meaning of the present disclosure in particular comprises monoclonal antibodies, polyclonal antibodies, as well as multi-specific antibodies.

In the context of one embodiment, the concentration can comprise the following steps:

binding of the analyte(s) to binder molecules, immobilization of the binder molecule-analyte complex, removal of unbound constituents, removal of the bound analytes.

The binder molecules for the analyte can be present dissolved in the buffer in which the sample is taken up. Alternatively, binder molecules such as antibodies or complexing agents which bind specifically to the target analyte can be added to the sample solution. After the addition, fungal spores present are bound by the binder molecules and are present in solution as a complex or conjugate. The solution is then transferred to a further compartment of the buffer unit, where the binder molecule-analyte complex, in particular fungal spore-antibody conjugates, is immobilized. The complex of analyte and primary antibody can be bound by means of secondary antibodies already bound to the solid phase, which are immobilized covalently on a carboxylated surface by means of an amide bond by means of coupling reagents such as s-NHS and EDC (N-hydroxysulfo-succinimide and carbodiimide). In a further step, unbound molecules and constituents in the sample are removed. This can be carried out by the addition of a rinsing solution. The rinsing solution here in particular has the properties of complying with physiological conditions in order not to release the antigen-antibody bond and not to rinse away the target analyte, the mold spore. For this purpose, a buffer solution is in particular suitable which corresponds to the buffer solution in which the sample was taken up, but which contains no binder molecules. Finally, the bound analyte is detached again from the binder molecule. Preferably, mold spores bound to antibody are brought into solution again using an "elution buffer". An elution buffer is generally understood as meaning buffer solutions which release an analyte from an immobilized binding partner. For this purpose, buffers are to be chosen such that the antigen-antibody binding between mold spore and primary antibody is detached. This can be carried out, for example, by means of a variation of the pH, which influences the interaction between two proteins. In contrast to this, the covalently bonded secondary antibody remains bound to the solid phase. By the addition of an elution buffer, the analytes are separated from the binder molecules and are again present in solution. This solution is transferred to a measuring chamber or immunological test unit for further measurement.

In the context of one embodiment, the binder molecules can be antibodies (primary antibodies), which are directed against surface markers of mold spores such as β-glucans. If antigens such as β-glucans are determined which are in general characteristic of molds, a general enrichment of all mold spores contained in the sample takes place. In the context of a further embodiment, the binder molecules can be species-specific antibodies to mold spores, for example antibodies to surface antigens, which are characteristic for specific mold species. In this case, very specific mold species can be enriched or selected for the detection. Thus an antibody-based pre-purification in addition to a general enrichment of all mold spores contained in the sample can be extended from a general test for mold spores to a qualitative test for specific mold species by the use of the species-specific antibodies. In particular, the choice of the antibody can thus moreover decide whether a total signal concerning all mold spores contained in the sample or only a species-specific signal of a mold species is measured. The selection of the secondary antibody is dependent on the origin of the primary antibody. This means that when using a primary antibody from a mouse a secondary antibody directed against mouse antibody must be employed.

For measurement, the analyte concentration can be adjusted by means of defined volume addition of buffer solution. The analysis of the liquid sample is carried out and visualized by means of immunological tests. Using the immunological testing in step c), it can be tested for at least one component selected from the group consisting of: ergosterol, β-1,3-glucan, and markers species-specific for molds. In the context of one embodiment, the test result from step d) can corresponds to a total signal over a number of mold spores contained in the sample or to a species-specific signal of a mold species. To be able to match values measured in an interior space with reference values, the apparatus can also be used in the outdoor area so as to delineate mold fungi which typically occur in the interior area from those in the outdoor area.

BRIEF DESCRIPTION OF THE DRAWINGS

Further advantages and advantageous embodiments of the subjects according to the disclosure are illustrated by the drawings and explained in the following description. It is to be noted here that the examples and drawings are only of descriptive character and are not intended to restrict the disclosure in any form.

DETAILED DESCRIPTION

Figure 1:
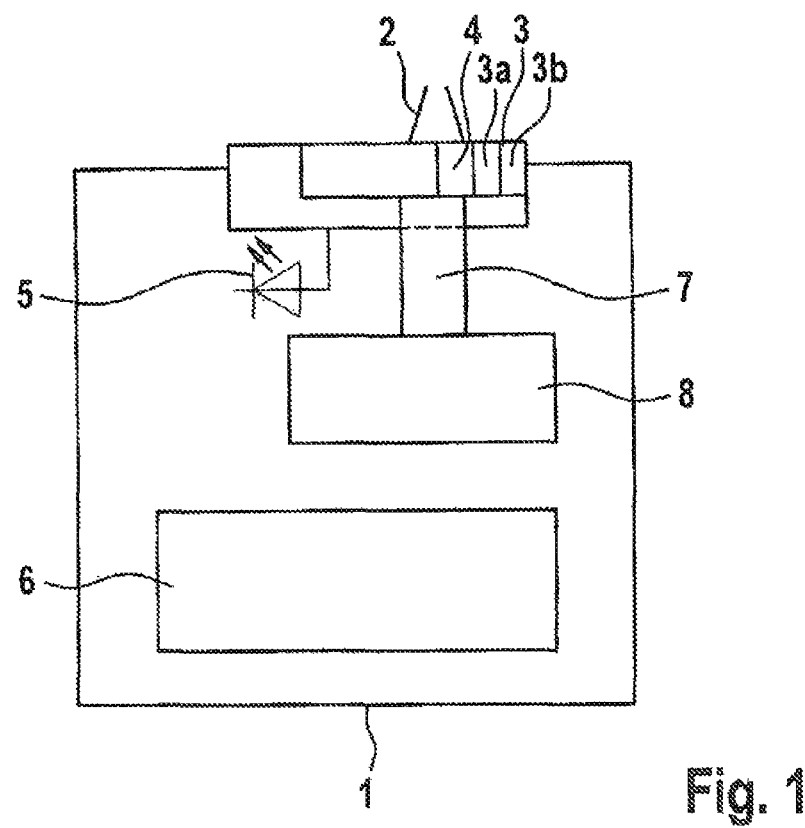
FIG. 1 shows a schematic view of an embodiment of a hand-held measuring instrument according to the disclosure.

FIG. 1 shows schematically an embodiment of the hand-held measuring instrument 1 according to the disclosure. The apparatus comprises a collection unit 2 for air and dust. The collection unit 2 comprises a pump or a fan as an intake module 8, and an air or dust channel 7. The essence of the collection unit 2 is an impactor or filter, on which the spores of the molds contained in the air are deposited and collected. The filter or impactor is configured as a single-use component. The buffer unit 3 has a first compartment 3a and a second compartment 3b. The buffer solutions are situated in the single-use cartridges and are arranged within the buffer unit 3. Within the first compartment 3a is arranged a cartridge containing a buffer, which contains antibodies to β-glucans of mold spores. The mold spores from air and dust are absorbed in this buffer solution after the conclusion of the collection process. The solution containing the mold spores bound to antibody is transferred to the second compartment, the binding compartment 3b. Within the second compartment 3b are arranged two further cartridges containing a buffer without antibody and an elution buffer. Furthermore, the second compartment 3b contains a solid phase containing secondary antibody bound via a carboxylated surface for the immobilization of the antibody-mold complex. After rinsing of the solid phase with buffer without binder molecules for the removal of unbound constituents, the bound mold spores are detached by addition of the elution buffer. The elution buffer containing the now concentrated mold spores is transferred to the immunological test unit 4. Within the test unit 4 is arranged a single-use immunoassay for the fungal spores. The evaluation unit 5 comprises optical evaluation optics. In addition to the necessary evaluation electronics, the hand-held measuring instrument 1 moreover has a control panel 6 or display, with which the results of the measurement are displayed.

The hand-held measuring instrument for carrying out the detection procedure contains a battery-operated filtration device with an air intake flow of about 100 l/min. The particles>0.5 μm found in the airflow are retained by a suitable filtration membrane and collected. The filtration attachment consists of a suction nozzle and a filtration membrane and is integrated as a plastic-based single-use component together with three buffer cartridges and the immunological rapid test. Before the air particle collection, this disposable unit is inserted in the hand-held measuring instrument. The air particle collection takes place over a few minutes.

Figure 2:
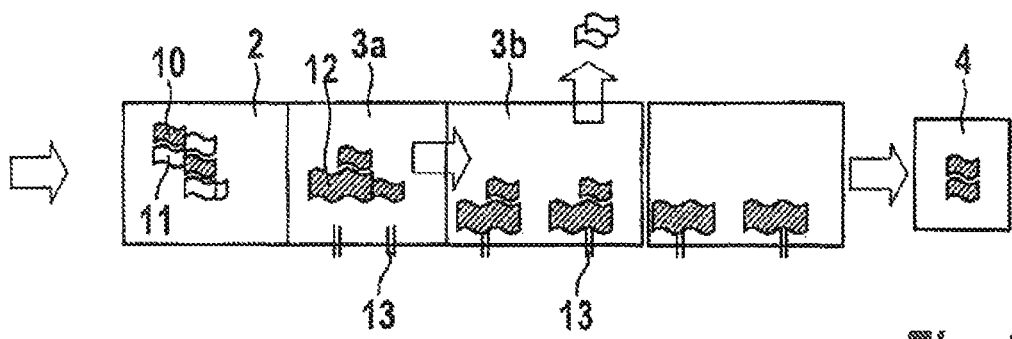
FIG. 2 shows a schematic reproduction of the procedure steps of concentration by means of analyte-specific binder molecules.

FIG. 2 shows a schematic reproduction of the procedure steps of concentration by means of analyte-specific binder molecules. The particles sucked in are collected in a collection chamber 2 of the hand-held measuring instrument. Next, the first cartridge containing a buffer solution is broken open by pushbutton pressure. The buffer solution provides physiological conditions for mold spores. In the buffer, primary antibodies are present dissolved as binder molecules, which are directed specifically against β-glucans as surface markers of mold spores. The buffer solution thereby reaches the filtration membrane and the collected analyte 10 and non-analyte 11 are suspended in the solution in the first compartment 3a of the buffer unit. Mold spores present are bound specifically by the primary antibodies 12 and are present in solution as a complex. The solution is transferred to the binding compartment 3b by means of pushbutton pressure.

Secondary antibodies 13 bound covalently to a carboxylated surface as an amide bond are already present in compartment 3b by means of coupling reagents such as s-NHS and EDC (N-hydroxysulfosuccinimide and carbodiimide). By pushbutton pressure, the second cartridge containing buffer solution, which is free of binder molecules, is now broken open. This buffer solution likewise maintains physiological conditions in order not to dissolve the antigen-antibody bond and not to rinse away the mold spores. For example, this buffer solution corresponds in its composition to the first buffer solution, but contains no primary antibodies. Unbound constituents 11 are removed by the addition, while the antigen-antibody complexes remain immobilized on the solid phase. After the rinsing, a third cartridge containing elution buffer is broken open by means of further pushbutton pressure. The elution buffer differs, for example, in pH from the buffers which are used for the uptake of the sample and for rinsing the solid phase. The antigen-antibody bond is separated by the addition of the elution buffer and the mold spores are detached from the binder molecules. The secondary antibodies covalently immobilized on the solid phase remain bound. The solution now contains a pre-purified sample, in which the target analyte was concentrated selectively by the antibody binding. By means of a defined volume addition of the elution buffer, the analyte concentration in the solution for measurement can be adjusted. This is likewise controllable manually by means of pushbutton pressure.

By means of further pushbutton pressure, the sample in which the mold spores are now present in solution again reaches the receiving surface of the immunological rapid test based on a multi-analyte-capable lateral flow test (LFT) in the immunological test unit 4. The labeled detection antibodies are found immobilized on the receiving surface. In the presence of the analyte to be detected, antigen-antibody conjugates bind to the designated detection areas of the evaluation unit. The optically read measurements of the various analytes, which correspond to the ergosterol/beta-1, 3-glucan content, are transferred to a microcontroller, which on the basis of the stored calibration data and the aspirated amount of air converts the measurements into the respective mold spore number per cubic metre of aspirated air. To obtain a better quantitative result and to check the correct test procedure, a reference area of the filter membrane can additionally be evaluated.

Depending on the choice of the antibody during the concentration, a total signal over all mold spores contained in the sample or a species-specific signal of a certain mold species is measured.

The output of the result takes place on a control panel or display. Moreover, the user obtains the information of whether molds were found, i.e. ergosterol or beta-1,3-glucan could be detected, and whether interior space-specific species were found. The measurements can be indicated directly as the spore number per cubic metre of collected air, or can already go through an assessment. For this purpose, an assessment scheme is stored in the measuring instrument, using which the measurements are calibrated. After termination of the measurement or before the next measurement, the single-use component is removed from the hand-held apparatus.

What is claimed is:

1. A method for detecting hidden mold damage in interior spaces using a hand-held measuring instrument, the method comprising:
   collecting an interior space sample;
   taking up the sample in a buffer;
   concentrating at least one analyte in the sample taken up in the buffer by binding the at least one analyte to analyte-specific antibodies in a first compartment of the hand-held measuring instrument so as to form antibody-analyte complexes;
   transferring the antibody-analyte complexes to a second compartment of the hand-held measuring instrument, wherein the second compartment comprises immobilized secondary antibodies capable of binding the analyte-specific antibodies so as to immobilize the antibody-analyte complexes via the immobilized secondary antibodies, and wherein the at least one analyte is at least one mold spore;
   removing unbound constituents;
   eluting the analytes from the analyte-specific antibodies;
   detecting the eluted analytes using an immunological test within the hand-held measuring instrument;
   evaluating the immunological test; and
   displaying a result of the evaluated test, thereby detecting hidden mold damage in the interior space.

2. The method of claim 1, wherein the analyte-specific antibodies are directed against surface markers of mold spores.

3. The method of claim 2, wherein the surface markers are β-glucans.

4. The method of claim 1, wherein the analyte-specific antibodies are species-specific antibodies to mold spores.

5. The method of claim 1, wherein the result of the evaluated test corresponds to one of: (i) a total signal for a number of mold spores contained in the sample and (ii) a species-specific signal of a mold species.

6. The method of claim 1, wherein the result of the evaluated test corresponds to a total signal for a number of mold spores contained in the sample.

7. The method of claim 1, wherein the secondary antibodies are immobilized on a solid phase of the second compartment.

* * * * *